(12) United States Patent
Lenor et al.

(10) Patent No.: US 10,366,505 B2
(45) Date of Patent: Jul. 30, 2019

(54) METHOD AND CONTROL DEVICE FOR PROCESSING AT LEAST ONE IMAGE REPRESENTING A HALATION, AND IMAGE RECORDING SYSTEM

(71) Applicant: Robert Bosch GmbH, Stuttgart (DE)

(72) Inventors: Stephan Lenor, Stuttgart (DE); Ulrich Stopper, Gerlingen (DE)

(73) Assignee: ROBERT BOSCH GMBH, Stuttgart (DE)

( * ) Notice: Subject to any disclaimer, the term of this patent is extended or adjusted under 35 U.S.C. 154(b) by 130 days.

(21) Appl. No.: 15/612,639

(22) Filed: Jun. 2, 2017

(65) Prior Publication Data

US 2018/0018789 A1 Jan. 18, 2018

(30) Foreign Application Priority Data

Jul. 18, 2016 (DE) .................. 10 2016 213 059

(51) Int. Cl.
| | |
|---|---|
| *G06T 7/11* | (2017.01) |
| *G06T 7/60* | (2017.01) |
| *G01N 15/02* | (2006.01) |
| *G01N 21/53* | (2006.01) |
| *G06K 9/46* | (2006.01) |

(52) U.S. Cl.
CPC .......... *G06T 7/60* (2013.01); *G01N 15/0227* (2013.01); *G01N 21/53* (2013.01); *G06K 9/4604* (2013.01); *G06K 9/4661* (2013.01); *G06T 7/11* (2017.01)

(58) Field of Classification Search
CPC ...... G06K 9/4604; G06K 9/4661; G06T 7/60; G06T 7/11; G01N 15/0227; G01N 21/21; G01N 21/53; G01N 2021/177
See application file for complete search history.

(56) References Cited

U.S. PATENT DOCUMENTS

| | | | |
|---|---|---|---|
| 2014/0029790 A1* | 1/2014 | Gallen | G01N 21/538 382/103 |
| 2015/0061493 A1 | 3/2015 | Jeromin et al. | |
| 2015/0256733 A1* | 9/2015 | Kanamori | H04N 5/2354 348/234 |
| 2016/0148073 A1* | 5/2016 | Uffenkamp | G06T 3/4038 348/148 |
| 2017/0357881 A1* | 12/2017 | Hoshino | G06T 1/00 |

FOREIGN PATENT DOCUMENTS

DE 10303046 A1 10/2004

* cited by examiner

*Primary Examiner* — Ali Bayat
(74) *Attorney, Agent, or Firm* — Norton Rose Fulbright US LLP; Gerard Messina (57) ABSTRACT

A method for processing an image representing at least one halation. The image is read in via an interface to an image recording device. In addition, using the image an intensity distribution representing the halation is ascertained. The intensity distribution is then analyzed in order to determine a surface-shaped distribution of particles in the region of acquisition of the image recording device as the cause of the halation, and to distinguish it from a volume-shaped distribution of particles.

22 Claims, 9 Drawing Sheets

METHOD AND CONTROL DEVICE FOR PROCESSING AT LEAST ONE IMAGE REPRESENTING A HALATION, AND IMAGE RECORDING SYSTEM

CROSS REFERENCE

The present application claims the benefit under 35 U.S.C. § 119 of German Patent Application No. DE 102016213059.5 filed on Jul. 18, 2016, which is expressly incorporated herein by reference in its entirety.

FIELD

The present invention relates to a device and a method FOR processing at least one image representing a halation. The present invention also relates to a computer program.

Conventional methods are available for determining the causes of visual limitations in a camera image.

SUMMARY

The present invention provides an example method for processing an image representing at least one halation, a control device that uses this method, and an image recording system. Through the measures described herein, advantageous developments and improvements of the device are possible.

An example method in accordance with the present invention is presented for processing an image representing at least one halation, the method including the following steps:

reading in the image via an interface to an image recording device;

ascertaining an intensity distribution representing the halation, using the image; and analysis of the intensity distribution in order to determine a surface-shaped distribution of particles in the region of acquisition of the image recording device as the cause of the halation.

A halation can be understood as a light collar or ring. The halation can be caused for example by diffraction or scattering of light beams emanating from a light source on atmospheric particles, for example in the form of fog, smoke, dust, rain, or snow, or on surface-bound particles, for example in the form of condensation on a pane. The origin of halations can be described for example using the theory published in 1908 by Gustav Mie, and later named for him, concerning light scattering on spherical particles.

An image can be understood as an individual image or an image series of a plurality of individual images. The image recording device can be an optical sensor, such as a photographic camera or video camera. The image recording device can for example be part of an environmental sensor system of a motor vehicle or of a video monitoring system of a building. An intensity distribution can be understood as a distribution of intensities of radiation surrounding the light source. For example, the intensity distribution can be a distribution of radiation intensities along a radius going out from a midpoint of the light source. The intensity distribution can be checked for maxima and minima, for example in the step of analysis, in order to determine the surface particle distribution on the basis of the maxima or minima. Through the analysis of the intensity distribution, the surface particle distribution can be distinguished from a volume-shaped distribution of particles.

For example, a surface particle distribution can be understood as a distribution of particles along a surface, such as a surface of a light-transparent element situated in the region of acquisition, such as a pane or a segment of the housing of the image recording device. The surface shape of the particle distribution can for example result from the fact that the particles, such as small drops of water or dirt particles, are situated in a common plane in the manner of a layer. In particular, the particles can be bound on the surface. A region of acquisition can be understood as a region that can be acquired by the image recording device in order to record the image.

The approach presented here is based on the recognition that through an analysis of an intensity distribution in a camera image the cause of a halation, and thus of a visual limitation in the camera image, can be determined in a targeted fashion. Here, information can be obtained concerning a spatial distribution of particles that cause scattering of the light and thus lead to the formation of the halation. Thus, on the basis of the spatial distribution a halation caused by microscopically small water droplets, ice crystals, or dust particles on a pane surface can for example be inferred as the cause of the visual limitation. Such a halation caused by a surface-shaped distribution of particles can also be referred to as a surface halation. The determination of a cause of a visual limitation in a camera image based on such an analysis of the halation has the advantage that a reliable distinction can be made between atmospheric visual limitations and visual limitations on a pane surface. Thus, depending on the visual limitation, countermeasures can be introduced, for example with the goal of removing the particles.

According to a specific embodiment, in the step of analysis the cause of the halation can be determined by classifying the intensity distribution on the basis of a first class assigned to the surface-shaped particle distribution and a second class assigned to a volume-shaped distribution of particles. A volume-shaped distribution of particles can be understood as a spatial distribution of particles in the atmosphere, such as fog, smog, smoke, dust, sand, pollen, small ice crystals, rain, snow, or hail. Through this specific embodiment, a reliable distinction between surface-shaped and particle-shaped particle distribution is enabled with a relatively low computing outlay.

According to a further specific embodiment, in the step of ascertaining the intensity distribution is ascertained as a function of a radial distance from a light source assigned to the halation. A radial distance of an arbitrary image point can be understood as its distance in the image to an image point representing the light source. This specific embodiment enables an efficient evaluation of the intensity distribution, for example through comparison of the measured intensity distribution with a far-field angular distribution of a scatter process, based on the Fraunhofer diffraction.

In addition, the method can include a step of extracting at least one item of processing information from the intensity distribution. Here, in the step of analysis the processing information can be analyzed in order to determine the surface-shaped particle distribution as the cause of the halation. An item of processing information can be understood for example as a quantity of information that is reduced relative to a quantity of information of the intensity distribution. This specific embodiment offers the advantage of a particularly fast analysis of the intensity distribution.

It is also advantageous if, in the step of extracting, at least one radial intensity profile that represents the intensity distribution as a function of the radial distance is extracted as the item of processing information. An intensity profile can be understood for example as a curve, or set of curves, representing the intensity distribution. In this way, the analysis of the intensity distribution can be simplified and accelerated.

In addition, in the step of analysis the surface-shaped particle distribution is determined as the cause of the halation if the intensity distribution has a main maximum and at least one secondary maximum. A main maximum can be understood for example as an absolute maximum of the intensity distribution. Correspondingly, a secondary maximum can be understood as a relative maximum of the intensity distribution. Through this specific embodiment, the surface-shaped particle distribution can be ascertained with a low computing outlay.

Conversely, in the step of analysis for example the volume-shaped particle distribution can be determined as the cause of the halation if the intensity distribution does not have a secondary maximum.

According to a further specific embodiment, the method includes a step of determining a particle size or, in addition or alternatively, a particle size distribution of the particles as a function of the intensity distribution. In this way, additional information can be obtained about the particles and their distribution.

For example, in the step of determining, the particle size can be determined as a function of a distance between the main maximum and the secondary maximum. In addition or alternatively, here the particle size distribution can be determined as a function of a width of the main maximum or of the secondary maximum. In this way, the particle size, or the particle size distribution, can be determined quickly and efficiently.

For example, in the step of determining the particle size or the particle size distribution can be respectively determined when, in the step of analysis, the surface-shaped particle distribution, and not the volume-shaped one, is determined as the cause of the halation.

It is also advantageous if, in a step of acquisition, results of the analysis over a specified time span are acquired in order to obtain a statistical view of the results of the analysis. Here, in a step of robustification, the analysis can be robustified using the statistics. In this way, sensitivity to disturbing variables can be reduced in the analysis of the intensity distribution.

In addition, in the step of ascertaining, using the image a wavelength distribution representing the halation can be ascertained. Here, in the step of analysis in addition the wavelength distribution can be analyzed in order to determine the surface-shaped particle distribution as the cause of the halation. For example, the wavelength distribution can be used in the step of analysis to plausibilize the particle distribution ascertained on the basis of the intensity distribution. In this way, the reliability of the method can be increased.

In addition, the method can include a step of producing a control signal for controlling a particle removal device for removing the particles as a function of the particle distribution. The particle removal device can be for example a heating device for heating a pane or a windshield wiper. Through this specific embodiment, visual limitations in the image can be efficiently removed.

This method can be implemented for example in software or hardware, or in a mixed form of software and hardware, for example in a control device.

The approach presented here provides in addition a control device that is fashioned to carry out, control, or realize the steps of a variant of a method presented here in corresponding devices. Through this variant embodiment of the present invention in the form of a control device as well, the underlying object of the present invention can be achieved quickly and efficiently.

For this purpose, the control device can have at least one computing unit for processing signals or data, at least one storage unit for storing signals or data, at least one interface to a sensor or to an actuator for reading in sensor signals from the sensor or for outputting control signals to the actuator, and/or at least one communication interface for reading in or outputting data that are embedded in a communication protocol. The computing unit can be for example a signal processor, a microcontroller, or the like, and the storage unit can be a flash memory, an EPROM, or a magnetic storage unit. The communication interface can be fashioned to read in or output data wirelessly and/or in wire-bound fashion, and a communication interface that can read in or output wire-bound data can for example electrically or optically read in these data from a corresponding data transmission line or output them to a corresponding data transmission line.

In the present context, a control device can be understood as an electrical device that processes sensor signals and outputs control and/or data signals as a function thereof. The control device can have an interface that can be fashioned as hardware and/or as software. In the case of a realization as hardware, the interfaces can for example be part of a so-called system ASIC that contains a wide variety of functions of the control device. However, it is also possible for the interfaces to be separate integrated circuits or to be made up at least partly of discrete components. In the case of a realization as software, the interfaces can be software modules present for example on a microcontroller alongside other software modules.

Finally, the approach described here provides an image recording system having the following features:

an image recording device for recording at least one image representing a halation; and a control device according to a specific embodiment described above, the control device being fashioned to determine a surface-shaped distribution of particles in the region of acquisition of the image recording device as the cause of the halation.

The image recording system can for example be an environmental sensor system of a motor vehicle or a video monitoring system of a building. Such an image recording system offers the advantage of a precise and efficient recognition of a cause of a halation in the image.

According to a specific embodiment, the image recording system includes a particle removal device for removing the particles. Here, the control device can be fashioned to control the particle removal device as a function of the particle distribution. In this way, the particles can be efficiently removed when a surface-shaped particle distribution is recognized.

Exemplary embodiments of the present invention are shown in the drawings and are explained in more detail below.

DETAILED DESCRIPTION OF EXAMPLE EMBODIMENTS

In the following description of advantageous exemplary embodiments of the present invention, identical or similar reference characters are used for elements shown in the various Figures and having similar function, and repeated description of these elements is omitted.

Figure 1:
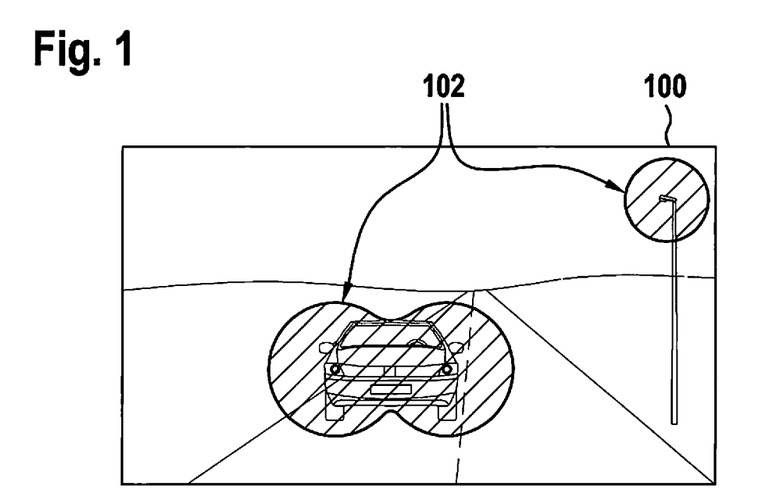
FIG. 1 shows a schematic representation of an image having halations.

FIG. 1 shows a schematic representation of an image 100 having halations 102. Halations 102 are caused for example by dense fog. The luminance decreases monotonically going out from the center of a respective light source of halations 102.

Figure 2:
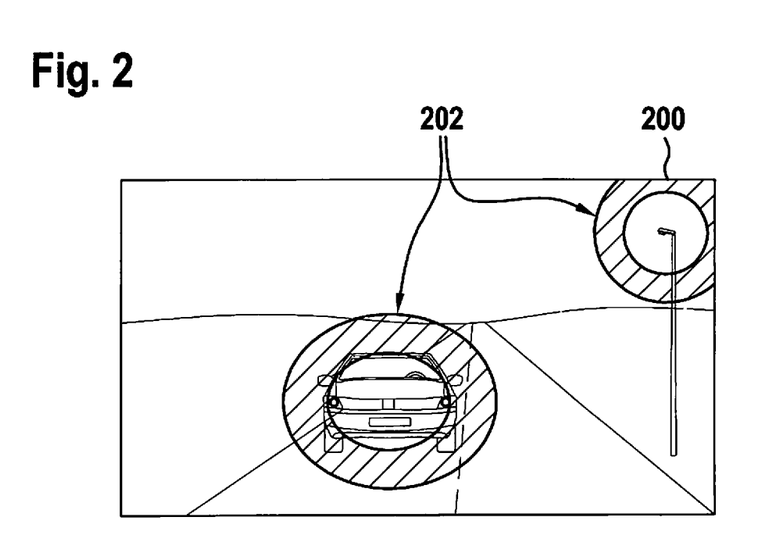
FIG. 2 shows a schematic representation of an image having halations.

FIG. 2 shows a schematic representation of an image 200 having halations 202. Differing from FIG. 1, the halations 202 shown in FIG. 2 are caused by a condensation having a broader droplet size distribution, for example by condensation of moist air on a cold pane over a longer period of time. In contrast to the halations of FIG. 1, here an annular structure can be seen.

Figure 3:
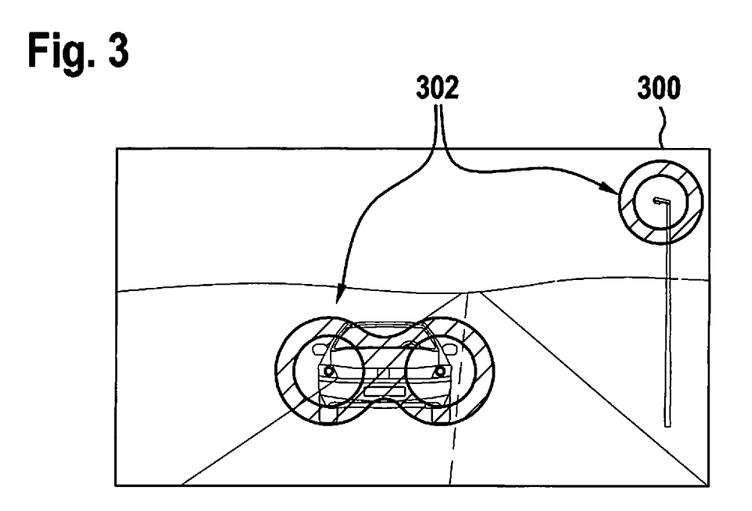
FIG. 3 shows a schematic representation of an image having halations.

FIG. 3 shows a schematic representation of an image 300 having halations 302. Halations 302 are caused by condensation with a narrow droplet size distribution and relatively large droplets, as is the case for example shortly after the thawing of ice by a windscreen heater. Here as well, an annular structure can be seen.

Figure 4:
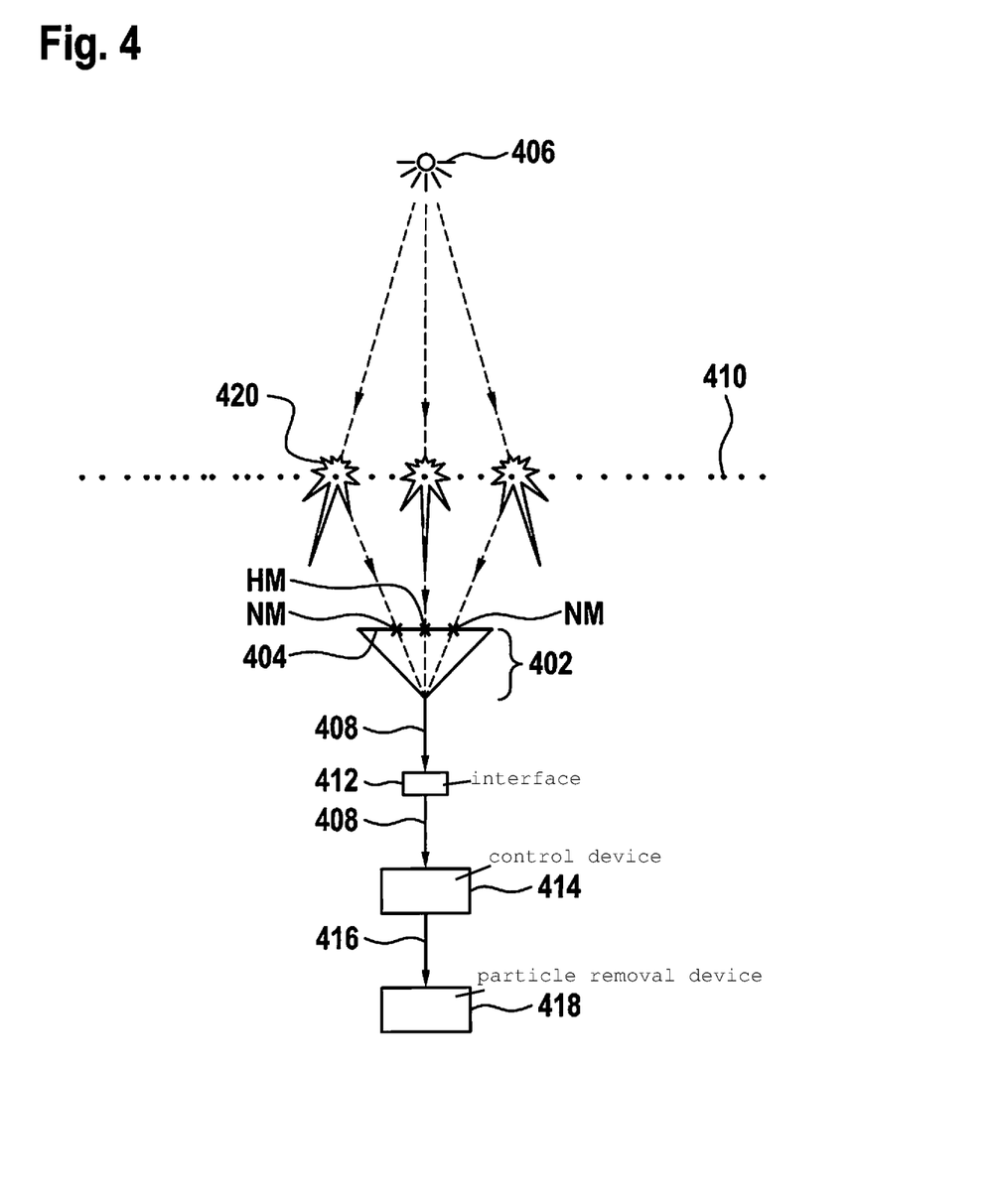
FIG. 4 shows a schematic representation of an image recording system according to an exemplary embodiment.

FIG. 4 shows a schematic representation of an image recording system 400 according to an exemplary embodiment. Image recording system 400 includes an image recording device 402, also called a detector, having an image plane 404. In the angle of acquisition of image recording device 402 there is situated a light source 406. Image recording device 402 is set up to record an image 408 of the angle of acquisition; light source 406, as well as particles 410 situated between light source 406 and image recording device 402, cause a halation in image 408. The halation can be for example one of the halations as described above on the basis of FIGS. 2 and 3. Image recording device 402 is connected via an interface 412 to a control device 414 that is fashioned to receive image 408 from image recording device 402. Control device 414 uses image 408 to ascertain an intensity distribution in image 408 representing the halation. Subsequently, control device 414 analyzes the intensity distribution in order to ascertain a distribution of particles 410 and thus a cause of the halation. According to the exemplary embodiment shown in FIG. 4, particles 410 are configured in a surface shape in a thin layer. Correspondingly, control device 414 ascertains a surface-shaped distribution of particles 410 as the cause of the halation. Thus, the halation is a surface halation, i.e. a visual limitation caused by articles adhering to a surface.

According to an exemplary embodiment, control device 414 is fashioned to output a control signal 416 for controlling a particle removal device 418, such as a windshield heater or wiper, as a function of the ascertained particle distribution. For example, control device 414 outputs control signal 416 when control device 414 has ascertained the surface-shaped particle distribution as the cause of the halation.

Expressed generally, control device 414 is used to identify the cause of particular visual limitations in image 408. The identification of the cause for example enables camera software or hardware, or an overall system including a camera, to adequately react to the visual limitation.

The visual limitations are halations, or halos (not to be confused with the German term "Halo," which refers to halations produced specifically by atmospheric ice crystals). A halation arises whenever the light of a compact light source 406 in a darker environment is scattered on a large quantity of particles 410 before impinging on the optical mechanism of an imaging detector such as image recording device 402 shown in FIG. 4. Particles 410 are here either solid, such as ice crystals or pollen, or liquid, such as water droplets. In the recorded image 408, the halation then appears as a bright, usually rotationally symmetrical veil that surrounds light source 406 in its immediate vicinity. As a rule, the occurrence of halations interferes with the intended purpose of image recording device 402 and recorded image 408. The covering of the dark background with the bright veil results in a contrast reduction that can for example make the recognition of object contours more difficult.

It is thus in the interest of the user to remove the cause of the visual limitation or, if removal is not possible, to take other measures through which negative consequences of the poor image quality can be reduced or entirely avoided. This reaction to the recognized visual limitation is particularly successful and has very few undesired side effects when applied to the cause of the halations. As part of the causal analysis, information is obtained about particles 410 that cause the scattering of the light. The spatial distribution, the size of particles 410, and the substance of which they are made can be of interest here.

In applications in which image recording device 402 is recording an outdoor scene, it may happen that halations are caused by an aerosol in the atmosphere, such as fog, smog, smoke, dust, sand, pollen, or small ice crystals, or by heavy precipitation, such as rain, snow, or hail. These effects, referred to in the following as atmospheric halations, cannot be directly removed by particle removal device 418. Instead, control device 414 for example takes the ascertained visual limitation in the form of the atmospheric halation into account in the further processing of the produced image information.

In applications in which image recording device 402 is positioned behind a transparent pane, for example behind a window or a windshield, it can happen that microscopically small droplets of liquid water, or similarly shaped and distributed solid ice crystals, form on the pane surface as particles 410, for example through condensation. Likewise, dust particles can accumulate as particles 410 on the pane surface. In such cases, specific halations can occur in the image that are also designated in the following as surface halations. In contrast to an atmospheric halation, a surface halation can be removed by particle removal device 418, for example by wiping or heating the pane.

Thus, using control device 414 in particular situations it is possible to determine that the halation in image 408 is not an atmospheric halation but rather a surface halation, and then to introduce a suitable countermeasure if warranted.

For example, through an automatic activation of particle removal device 418, a condensation or contamination of the pane can be removed. In addition, it can be prevented that particle removal device 418 is automatically activated in situations in which its use would have no effect, such as in the case of fog without a condensation on the pane, and that would possibly have undesired side effects, such as increased energy consumption due to the windshield heating, unnecessary heating of camera hardware, occlusion of view by the windshield wiper, or unnecessary wear on the windshield wiper.

According to an exemplary embodiment, control device 414 is fashioned to obtain information, using image 408, that enables the control device to identify individual halations in image 408 and to assign them to the classes "atmospheric halation," representing a volume-shaped particle distribution of articles 410, and "surface halation," representing the surface-shaped particle distribution.

For this purpose, control device 414 executes a corresponding program that is able to carry out this classification with the aid of image recording device 402. The approach described here also covers an automatic function of image recording system 400 through which a reaction adapted to a result of the classification is carried out, for example by particle removal device 418. For example, for the case in which the classification yields the result that the halation is a surface halation, the reaction includes the introduction of countermeasures against the visual limitation in the form of the surface halation. If the classification instead yields the result that the halation is an atmospheric halation, then the reaction for example includes an adaptation of the program behavior to the presence of the visual limitation in the form of the atmospheric halation.

The distinction between atmospheric visual limitations such as fog and visual limitations on a pane, in particular a windshield, as condensation, facilitates the targeted introduction of suitable reactions. This is an advantage because for example the countermeasures against a condensation usually include the activation of a heating, resulting in an increased energy consumption of the system and a shortened lifespan of the components. These negative effects can be reduced if control device 414 does not activate the heating if control device 414 recognizes that the cause of the visual limitation is not condensation but rather is fog.

As is schematically shown in FIG. 4, a main maximum HM and at least one secondary maximum NM of a phase function 420 of a scattering of the light emanating from light source 406 by the configuration of particles 410 in a thin layer are imaged at separate positions on image plane 404. According to an exemplary embodiment, control device 414 is fashioned to recognize the at least one secondary maximum NM on the basis of the intensity distribution, and as a result to determine the surface-shaped particle distribution as the cause of the halation.

Figure 5:
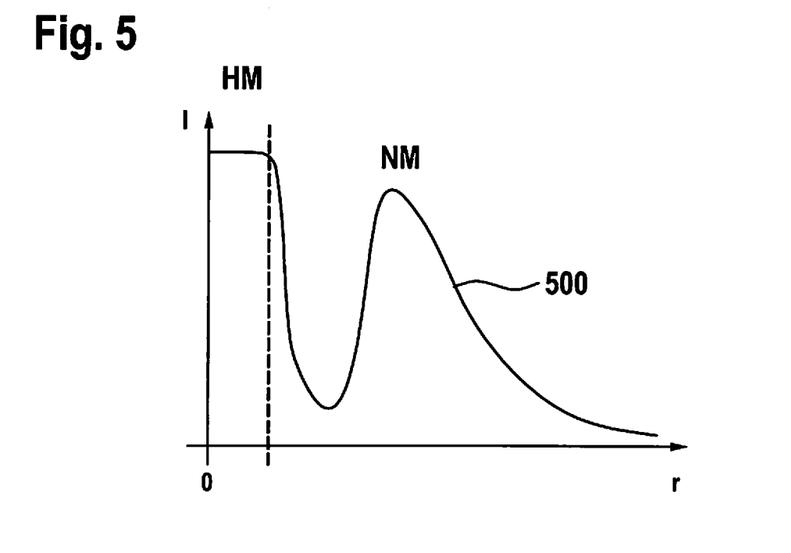
FIG. 5 shows a diagram representing an intensity distribution in an image from FIG. 4.

FIG. 5 shows a diagram representing an intensity distribution in an image from FIG. 4. Shown is a distribution curve 500 representing the intensity distribution with main maximum HM and secondary maximum NM. The intensity distribution shown in FIG. 5 is for example ascertained by control device as described above on the basis of FIG. 4. A dashed vertical line represents an edge of the light source in the image. On the ordinate, intensity I is plotted. The abscissa represents a radial distance r from the center of the light source. Distribution curve 500 thus represents a radial intensity distribution of a surface halation having main maximum HM at r=0 and having the clearly visible secondary maximum NM. Such a radial intensity distribution is produced for example by the halations described above on the basis of FIGS. 2 and 3.

Figure 6:
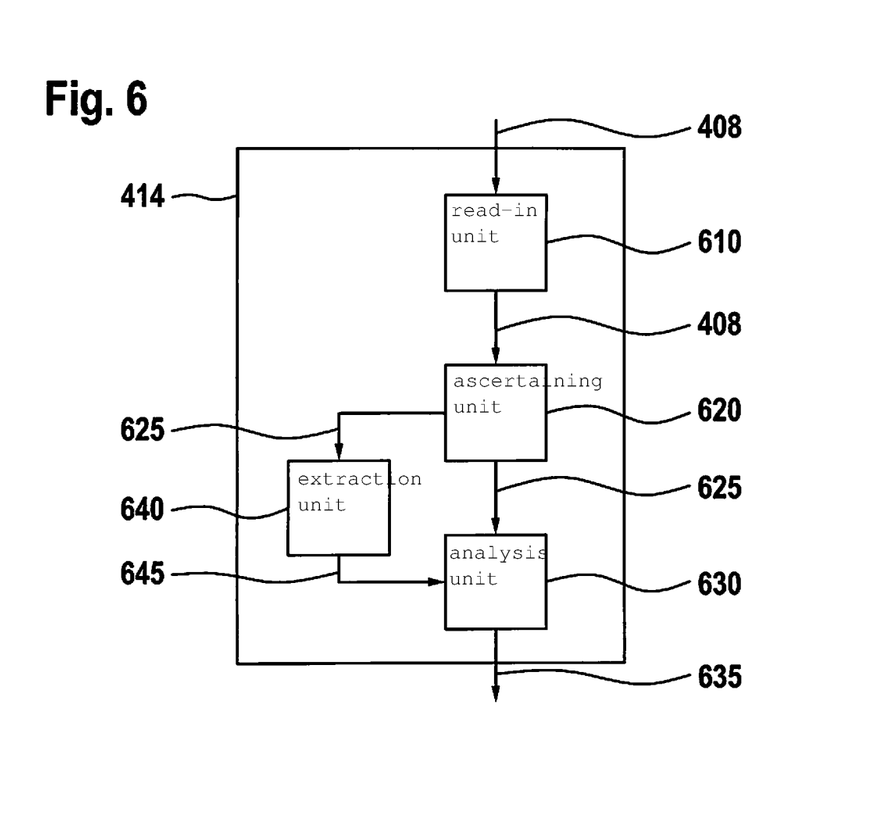
FIG. 6 shows a schematic representation of a control device according to an exemplary embodiment.

FIG. 6 shows a schematic representation of a control device 414 according to an exemplary embodiment, such as a control device as described above on the basis of FIGS. 4 and 5. Control device 414 includes a read-in unit 610 for reading in image 408 via the interface to the image recording device. An ascertaining unit 620 of control device 414 is fashioned to ascertain, using image 408, an intensity distribution representing the halation, and to transmit an item of intensity information 625 representing the intensity distribution to an analysis unit 630 of control device 414. Analysis unit 630 is fashioned to use intensity information 625, which for example represents a distribution curve described above on the basis of FIG. 5, to determine the surface-shaped distribution of the particles in the region of acquisition of the image recording device as the cause of the halation. As the result of the analysis of the intensity distribution, analysis unit 630 produces an item of halation information 635 representing the cause of the halation.

According to an exemplary embodiment, control device 414 includes an optional extraction unit 640 that is fashioned to extract, using intensity information 625, at least one item of processing information 645, for example at least one radial intensity profile that represents an intensity distribution as a function of a radial distance of the light source. Processing information 645 represents a quantity of information that is reduced compared to intensity information 625. Correspondingly, analysis unit 630 is fashioned to determine the particle distribution using processing information 645.

Figure 7:
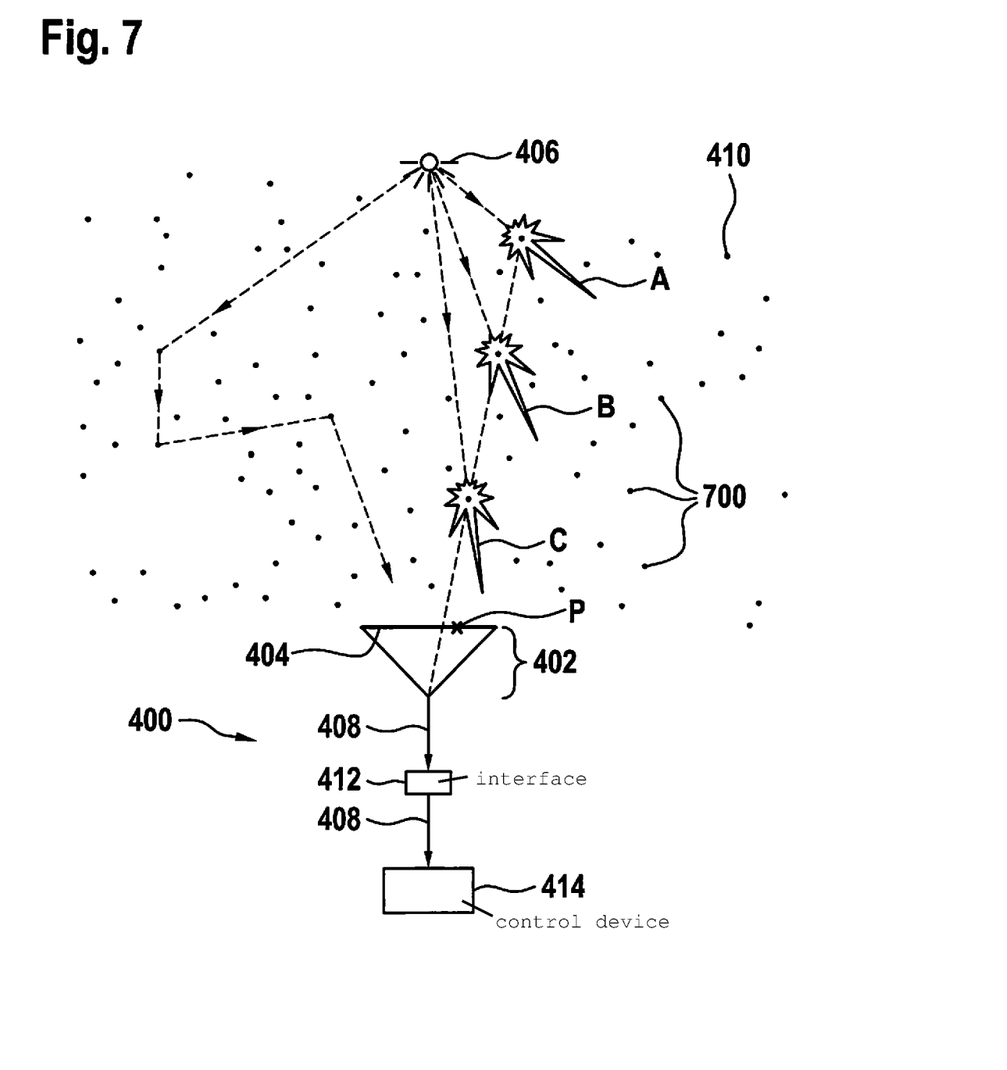
FIG. 7 shows a schematic representation of an image recording system according to an exemplary embodiment.

FIG. 7 shows a schematic representation of an image recording system 400 according to an exemplary embodiment. Image recording system 400 corresponds essentially to the image recording system described above on the basis of FIG. 4, with the difference that the particles here are not distributed in surface-shaped fashion, but rather are particles 700 distributed in a volume shape between light source 406 and image recording device 402. Through the distribution of particles 700 in a volume, image recording device 402 receives, from a single direction P, the light from different angles from phase functions A, B, C. The size of particles 700 can vary significantly. According to the exemplary embodiment shown in FIG. 7, control device 414 is fashioned to determine the volume-shaped particle distribution on the basis of the intensity distribution in image 408 as the cause of the halation in image 408, for example through a classification of the intensity distribution as described above on the basis of FIG. 4.

Figure 8:
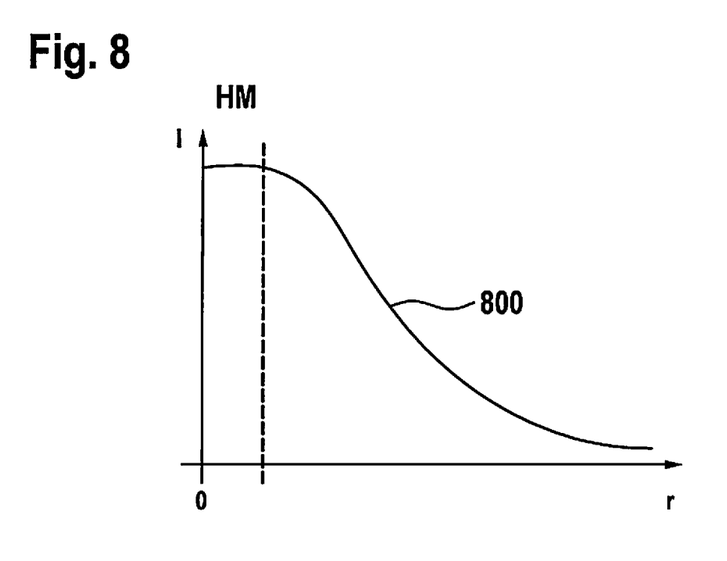
FIG. 8 shows a diagram representing an intensity distribution in an image from FIG. 7.

FIG. 8 shows a diagram representing an intensity distribution in an image from FIG. 7. Shown is a distribution curve 800 representing the intensity distribution, which, differing from FIG. 5, has only main maximum HM. Distribution curve 800 thus represents a radial intensity distribution of an atmospheric halation in which the main maximum and the secondary maximum are no longer clearly separated from one another. Such a radial intensity distribution is caused for example by a halation as described above on the basis of FIG. 1.

In the following, two exemplary embodiments of image recording system 400 are described again more precisely.

According to a first exemplary embodiment, image recording system 400 is realized having a video camera installed behind a windshield of a vehicle, as image recording device 402. Image recording device 402 is fashioned to monitor a region in front of the vehicle and in this way to enable various driver assistance functions. Thus, for example the vehicle can stay in its lane itself through autonomous steering processes. If the view of image recording device 402 is limited, then control device 414 analyzes the image stream of image recording device 402, using suitable camera software, and in this way ascertains that the visual limitation is caused either on the surface of the windshield or in the atmosphere in front of the vehicle. In the first case, control device 414 automatically activates a windshield heating in order to heat the windshield. In addition or alternatively, control device 414 briefly activates a windshield wiper in order to wipe the windshield. In this way, condensation that may be present is removed, or dirt is removed. In the second case, control device 414 informs the driver of the vehicle that the driver assistance functions are not available in their full scope because a visual limitation is present in the air in front of vehicle.

According to a second exemplary embodiment, image recording device 402 is realized as a video camera installed on a building, behind protective glass. Here, image recording device 402 is used to monitor a region in front of the building, thus enabling various safety-related functions. For example, security personnel can be informed if a person is situated in front of the building. If the view of image recording device 402 is limited, control device 414 ascertains, by analyzing the image stream of image recording device 402, whether the visual limitation is caused on the surface of the protective glass or in the atmosphere in front of the building. In the first case, control device 414 automatically activates a heating of the protective glass, thus removing a condensation that may be present. In the second case, control device 414 informs the security personnel that the monitoring functions are not available in their full scope because a visual limitation is situated in the air in front of the building.

Figure 9:
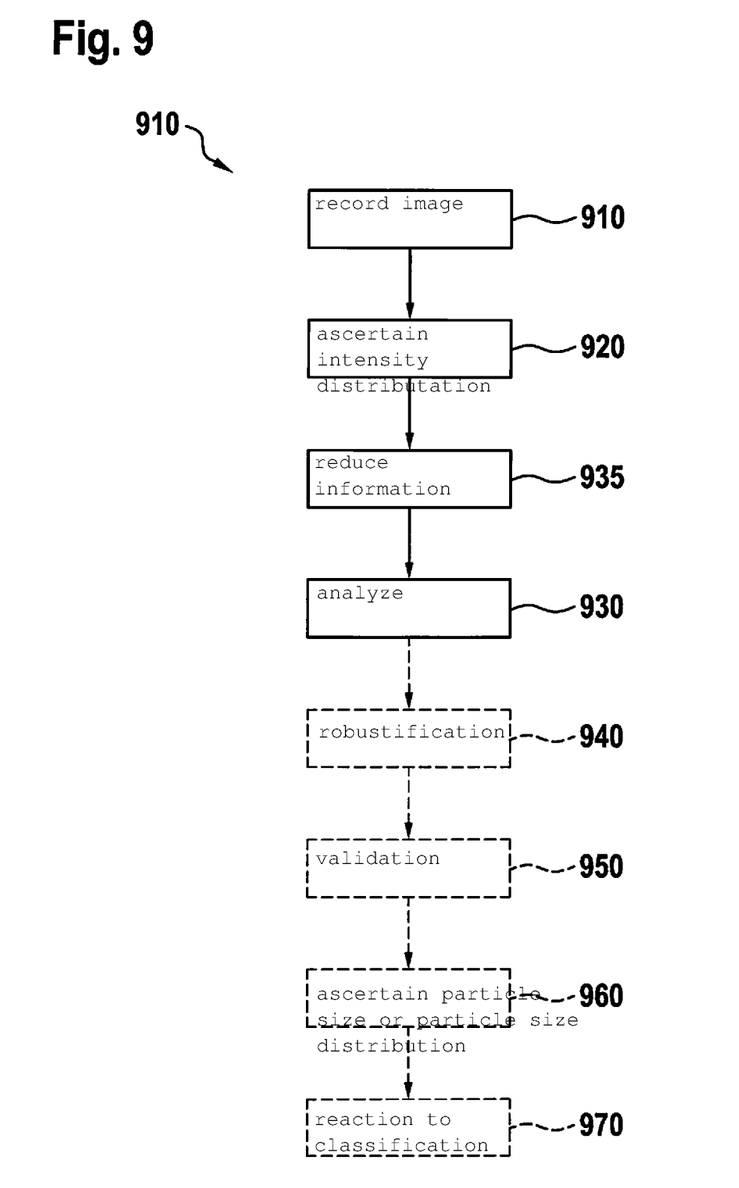
FIG. 9 shows a flow diagram of a method according to an exemplary embodiment.

FIG. 9 shows a flow diagram of a method 900 according to an exemplary embodiment. Shown is a method diagram for a general case of a processing of at least one image representing a halation. Method 900 can be carried out for example in connection with a control device described above on the basis of FIGS. 4 through 8 for determining the cause of visual limitations in camera images on the basis of the analysis of halations. Here, in a step 910 the image recorded by the image recording device, such as an individual image or series of images, is read in. For example, after being recorded the image is forwarded to a corresponding program in the control device. In a step 920, using the image the intensity distribution representing the halation, also called the halation appearance image, is ascertained. In a further step 930 the intensity distribution is analyzed in order to determine the particle distribution and thus the cause of the halation.

According to the exemplary embodiment shown in FIG. 9, following step 920 an optional step 935 is carried out in which the information representing the halation appearance image is reduced in order to obtain a reduced item of information as processing information. Here, in step 930 there takes place the analysis of the reduced information. As a result of the analysis, the reduced information is assigned to the class "atmospheric halation" or to the class "surface halation."

According to a further exemplary embodiment, in a step 940 following the analysis there takes place a robustification of the classification result using statistical information about results of the classification over a predefined time period.

In a further step 950, there optionally takes place the validation of the classification result on the basis of color information from the image recorded by the image recording device.

If in step 930 a surface halation is ascertained, then optionally in an additional step 960 a particle size of the particles or a particle size distribution is ascertained.

In a further optional step 970 there takes place a reaction to the classification result, for example by outputting the control signal for controlling particle removal device 418.

Figure 10:
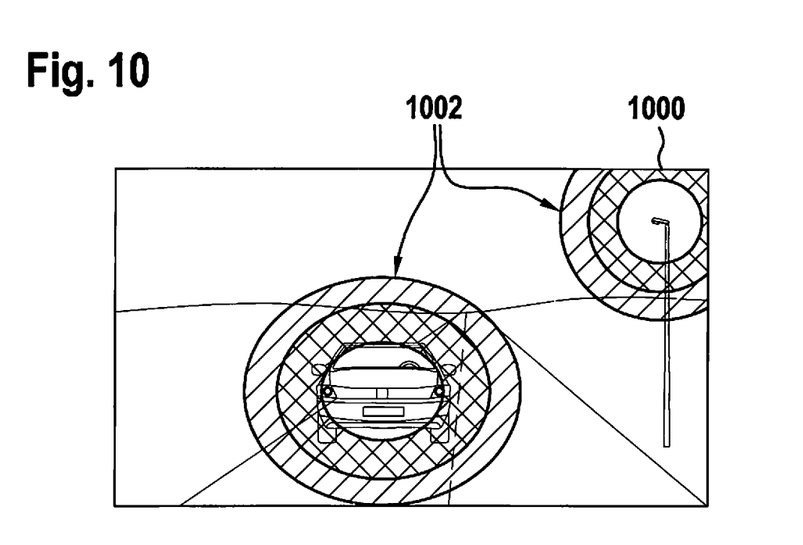
FIG. 10 shows a schematic representation of an image having halations.

FIG. 10 shows a schematic representation of an image 1000 having halations 1002. Image 1000 is a color image possibly recorded by an image recording device with a condensation, on the basis of FIGS. 4 through 9. Halations 1002 are annular surface halations whose outer side is red and whose inner side is blue.

Figure 11:
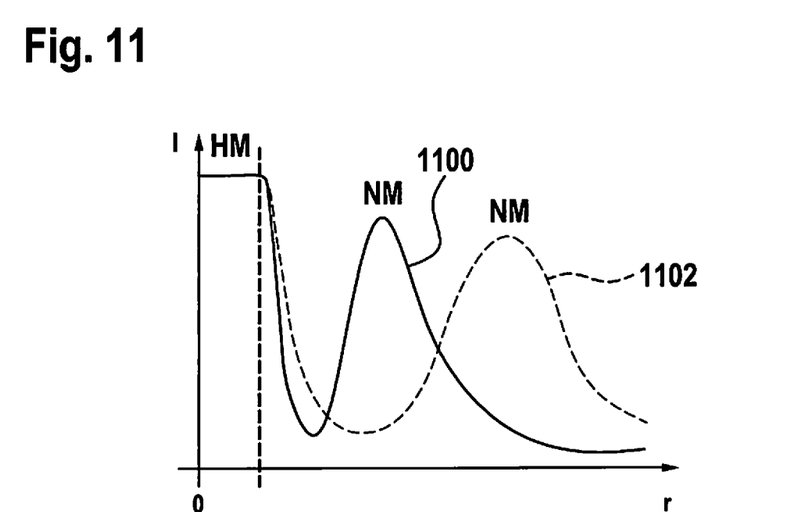
FIG. 11 shows a diagram representing an intensity distribution in an image from FIG. 10.

FIG. 11 shows a diagram representing an intensity distribution in an image from FIG. 10. Shown is a spectral dispersion of a surface halation from FIG. 10, with a first distribution curve 1100 representing light with a short wavelength and a second distribution curve 1102 representing light with a long wavelength. As is visible from FIG. 11, in the case of short-wavelength light of a surface halation in the image, secondary maximum NM is situated closer to the main maximum HM (r=0) than in the case of long-wavelength light.

Figure 12:
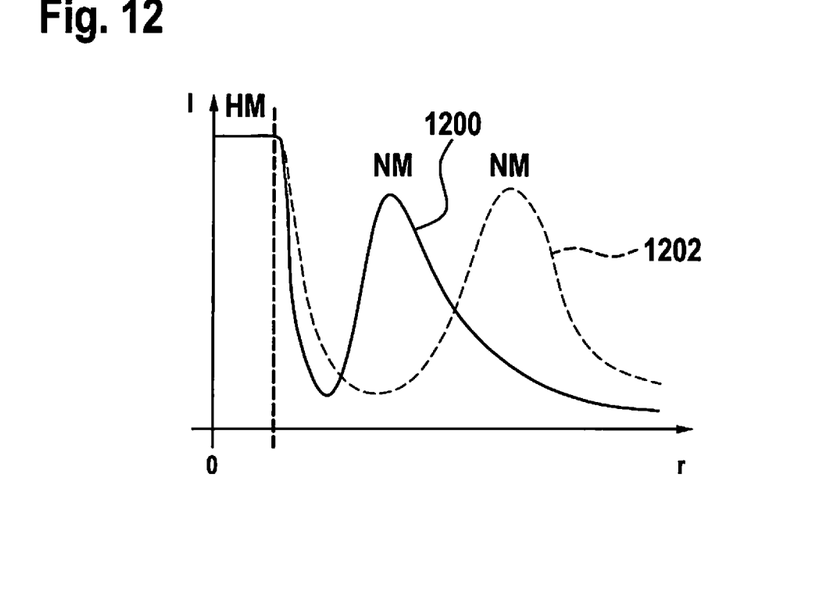
FIG. 12 shows a diagram representing an intensity distribution for analysis by a control device according to an exemplary embodiment.

FIG. 12 shows a diagram representing an intensity distribution for analysis by a control device according to an exemplary embodiment, such as a control device, as described above on the basis of FIGS. 4 through 11. Shown are a first distribution curve 1200 that represents a surface-shaped particle distribution of large particles, and a second distribution curve 1202 that represents a surface-shaped particle distribution of small particles. From FIG. 12 it can be seen that the secondary maximum NM of a surface halation in the image in the case of large particles is situated closer to the main maximum HM (r=0) than in the case of small particles.

Figure 13:
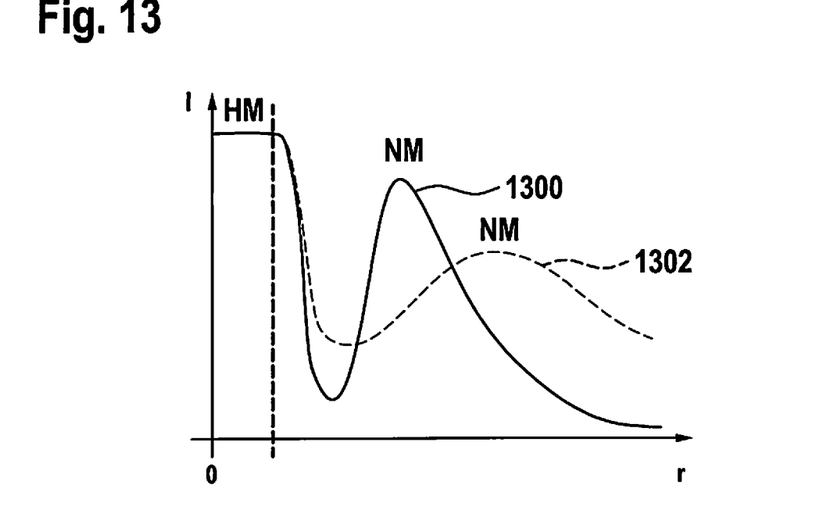
FIG. 13 shows a diagram representing an intensity distribution for analysis by a control device according to an exemplary embodiment.

FIG. 13 shows a diagram representing an intensity distribution for analysis by a control device according to an exemplary embodiment such as a control device as described above on the basis of FIGS. 4 through 12. Shown are a first distribution curve 1300, representing a narrow distribution of the particle sizes, and a second distribution curve 1302, representing a broad distribution of the particle sizes. In FIG. 13, it can be seen that a narrow particle size distribution results in a narrow secondary maximum NM, and a broad particle size distribution results in a broad secondary maximum NM.

In the following, the approach presented here is again explained using other words on the basis of FIG. 9.

First step 910 is the recording of an image by the image recording device. The image is forwarded to a corresponding program in the control device for processing.

In step 920, the program first ascertains the appearance image of halations in the image. This halation appearance image is made up of a set of pixel intensity values that represent a specific or average halation. In the simplest case, this set is identical with a segment of the original image that contains the surrounding environment of an intensity maximum.

The next step 935 is to reduce all information contained in the halation appearance image to a set of information that on the one hand is still suitable for the subsequent analysis and on the other hand is small enough to enable fast processing in the control device. Because the intensity distribution in a halation is in most cases approximately radially symmetrical, here the extraction of radial intensity profiles suggests itself. In the simplest case, such intensity profiles are obtained for example from the pixel intensities of a 1-D section through the maximum of the light source.

There follows the analysis of the reduced information in step 930. The result of the analysis is a classification of the halation appearance image into one of the two classes "atmospheric halation" and "surface halation." For this purpose, for example modeling predictions are used that are based on the Mie theory. Thus, for example the idealized far-field angular distribution of a scatter process, also called phase function, can be calculated via the Fraunhofer diffraction:

$$I(\Theta) \propto \left( \frac{(1 + \cos\Theta) \cdot J_1(x\sin\Theta)}{2\sin\Theta} \right)^2$$

Here, $I(\Theta)$ stands for the intensity of the far field for scatter angle $\Theta$.

$x=2\pi r/\lambda$ is the size parameter that relates particle circumference $2\pi r$ to the light wavelength $\lambda$.

$J_1$ is the first-order Bessel function.

This equation describes the diffraction portion of the $0^{th}$-order function from the Debye series, which is approximately equal to the diffraction pattern of a circular diaphragm having radius r. If the particles are situated only in a relatively thin layer between the light source and the observer, i.e. the image recording device, as is the case for example when there is a pane coated with condensation, then for the observer a specific annular halation, also called a corona, is visible. The radial distribution of this halation contains, in addition to main maximum HM, at least one minimum and a secondary maximum NM as described above on the basis of FIG. 5.

If, in contrast, the particles fill a larger volume between the light source and the observer, for example in the case of fog, then various effects occur that have the result that secondary maximum NM can no longer be separated from main maximum HM, so that no minimum is present in the radial distribution, as is shown in FIG. 8. Through the particle distribution in the volume, the observer acquires a plurality of scatter angles simultaneously when looking in a single direction. During their movement through the volume, the photons can be multiply scattered. The larger the volume is, the more likely it is that variations of the particle size can occur.

In step 930, in the analysis of the radial intensity profile, the existence of a secondary maximum is therefore sought. If the secondary maximum can be clearly recognized, then the halation is assigned to the class "surface halation." Otherwise, it is classified as "atmospheric halation."

All following steps, shown in dashed lines in FIG. 9, are optional. Thus, for example statistical information about the classification results over a predefined time span can be created, which can be used in step 940 to robustify the classification results.

In addition, in step 950 the wavelength-dependence of the scatter process can be used to validate the classification result. As shown in FIG. 11, in the case of surface halations secondary maximum NM is located further away from the main maximum the longer the wavelength of the light is. If the image recording device is fashioned to distinguish colors, then in the case of an actually present surface halation it can be assumed that regions of the secondary maximum situated further out have a larger red portion than do regions of the secondary maximum situated further in. This is shown schematically in FIG. 10. For example, in step 950 a class assignment already carried out can be revised if checking the color information yields a different wavelength distribution.

Via the radial intensity profile, in step 960 a rough estimation of the particle size can optionally be carried out. The smaller the particles are, the further removed secondary maximum NM is from main maximum HM. This is shown in FIG. 12. The greater the variance of the particle size is, the broader the main maximum and secondary maximum are, as can be seen from FIG. 13. The information about the particle size can for example be used later for a more precise matching of a reaction to the classification result, for example by setting, in the case of smaller water droplets, a shorter heating phase or a lower heating temperature in order to remove the condensation.

In the optional step 970, there takes place the reaction to the classification result. If a surface halation is recognized, then for example a countermeasure is carried out that removes the visual limitation. If, in contrast, an atmospheric halation is recognized, then the system is set to recognize that a visual limitation is present that cannot be removed, and that therefore reduced performance of the image recording device will have to be accepted for the time being.

If an exemplary embodiment includes an "and/or" linkage between a first feature and a second feature, this is to be read as meaning that according to a first specific embodiment the exemplary embodiment has both the first feature and the second feature, and according to a further specific embodiment the exemplary embodiment has either only the first feature or only the second feature.

What is claimed is:

1. A method comprising:
   a processor obtaining signals representing an image via an interface to an image recording device;
   the processor ascertaining an intensity distribution in the image signals, the intensity distribution representing a halation in the image;
   the processor analyzing the intensity distribution in order to determine that a surface-shaped distribution of particles lying on a surface that is in a region of acquisition of the image recording device is a cause of the halation; and
   responsive to the determination, the processor controlling a hardware execution of a physical response action.

2. The method as recited in claim 1, wherein, in the step of analyzing, the cause of the halation is determined through classification of the intensity distribution on the basis of a first class that is assigned to the surface-shaped particle distribution and a second class that is assigned to a volume-shaped particle distribution in air.

3. The method as recited in claim 1, wherein, in the step of ascertaining, the intensity distribution is ascertained as a function of a radial distance from a light source assigned to the halation.

4. The method as recited in claim 1, further comprising:
extracting at least one item of processing information from the intensity distribution, the processing information being analyzed, in the step of analyzing, in order to determine the surface-shaped particle distribution as the cause of the halation.

5. The method as recited in claim 4, wherein, in the step of extracting, at least one radial intensity profile that represents the intensity distribution as a function of the radial distance is extracted as the item of processing information.

6. The method as recited in claim 1, wherein the controlling includes providing a control signal that triggers a particle removal device to remove the particles from the surface.

7. The method as recited in claim 1, wherein the physical response action is a removal of the particles from the surface.

8. A method comprising:
a processor obtaining signals representing an image via an interface to an image recording device;
the processor ascertaining an intensity distribution in the image signals, the intensity distribution representing a halation in the image;
the processor analyzing the intensity distribution to identify a main maximum and at least one secondary maximum within the intensity distribution;
based on the main and secondary maximums, the processor identifying a distribution of particles in a region of acquisition of the image recording device that is causing the halation; and
responsive to the determination, the processor controlling a hardware execution of a physical response action.

9. The method as recited in claim 8, further comprising:
determining, as a function of the intensity distribution, at least one of a particle size and a particle size distribution of the particles.

10. The method as recited in claim 9, wherein, in the step of determining, at least one of: (i) the particle size is determined as a function of a distance between the main maximum and the secondary maximum, and (ii) the particle size distribution is determined as a function of a width of at least one of the main maximum and the secondary maximum.

11. The method as recited in claim 8, wherein the physical response action is a removal of the particles from a surface that is present in the region of acquisition.

12. The method as recited in claim 8, wherein the physical response action is a modification of a control by a vehicle drive assistance unit.

13. A method comprising:
a processor performing the following repeatedly over a time period:
obtaining signals representing an image via an interface to an image recording device;
ascertaining an intensity distribution in the image signals, the intensity distribution representing a halation in the image; and
analyzing the intensity distribution in order to determine a distribution of particles in a region of acquisition of the image recording device that is causing the halation;
the processor obtaining statistical information about the determined distributions;
the processor obtaining a particle distribution classification based on the statistical information; and
responsive to the classification, the processor controlling a hardware execution of a physical response action.

14. The method as recited in claim 13, wherein the physical response action is a removal of the particles from a surface that is present in the region of acquisition.

15. The method as recited in claim 13, wherein the physical response action is a modification of a control by a vehicle drive assistance unit.

16. A method comprising:
a processor obtaining signals representing an image via an interface to an image recording device;
the processor ascertaining a wavelength-specific intensity distribution in the image signals, the wavelength-specific intensity distribution representing a halation in the image;
the processor analyzing the wavelength-specific intensity distribution in order to determine a distribution of particles in a region of acquisition of the image recording device that is causing the halation; and
responsive to the determination, the processor controlling a hardware execution of a physical response action.

17. The method as recited in claim 16, wherein the physical response action is a removal of the particles from a surface that is present in the region of acquisition.

18. The method as recited in claim 16, wherein the physical response action is a modification of a control by a vehicle drive assistance unit.

19. A control device comprising:
an interface to an image recording device; and
a processor;
wherein the processor is configured to:
obtain, via the interface and from the image recording device, signals representing an image;
ascertain an intensity distribution in the image signals, the intensity distribution representing a halation in the image;
analyze the intensity distribution in order to determine that a surface-shaped distribution of particles lying on a surface that is in a region of acquisition of the image recording device is a cause of the halation; and
responsive to the determination, control a hardware execution of a physical response action.

20. The control device as recited in claim 19, wherein the physical response action is a removal of the particles from the surface.

21. A system comprising:
an image recording device for recording signals that represent an image; and
a control device that includes a processor, wherein the processor is configured to:
obtain the signals from the image recording device;
ascertain an intensity distribution in the image signals, the intensity distribution representing a halation in the image;
analyze the intensity distribution in order to determine that a surface-shaped distribution of particles lying on a surface that is in a region of acquisition of the image recording device is a cause of the halation; and
responsive to the determination, control a hardware execution of a physical response action.

22. The system as recited in claim 21, wherein the control device further includes a particle removal device and the responsive control by the processor is a control of the particle removal device to remove the particles from the surface.

* * * * *